United States Patent
Ma

(10) Patent No.: US 8,733,612 B2
(45) Date of Patent: May 27, 2014

(54) SAFETY METHOD FOR POWERED SURGICAL INSTRUMENTS

(75) Inventor: Yong Ma, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 342 days.

(21) Appl. No.: 12/853,039

(22) Filed: Aug. 9, 2010

(65) Prior Publication Data

US 2011/0036890 A1  Feb. 17, 2011

Related U.S. Application Data

(60) Provisional application No. 61/234,377, filed on Aug. 17, 2009.

(51) Int. Cl.
*A61B 17/10* (2006.01)
*A61B 17/04* (2006.01)

(52) U.S. Cl.
USPC ...................................... 227/175.2

(58) Field of Classification Search
USPC .............. 227/175.1–182.1; 606/75, 300, 138, 606/219
See application file for complete search history.

(56) References Cited

U.S. PATENT DOCUMENTS

| | | |
|---|---|---|
| 5,350,355 A | 9/1994 | Sklar |
| 5,383,880 A * | 1/1995 | Hooven ........................ 606/142 |
| 5,464,144 A | 11/1995 | Guy et al. |
| 5,531,744 A | 7/1996 | Nardella et al. |
| 5,575,799 A | 11/1996 | Bolanos et al. |
| 5,653,374 A | 8/1997 | Young et al. |
| 5,680,981 A | 10/1997 | Mililh et al. |
| 5,779,130 A | 7/1998 | Alesi et al. |
| 6,007,550 A | 12/1999 | Wang et al. |
| 6,063,095 A | 5/2000 | Wang et al. |
| 6,436,107 B1 | 8/2002 | Wang et al. |
| 6,443,973 B1 | 9/2002 | Whitman |
| 6,461,372 B1 | 10/2002 | Jensen et al. |
| 6,505,768 B2 | 1/2003 | Whitman |
| 6,533,157 B1 | 3/2003 | Whitman |
| 6,698,643 B2 | 3/2004 | Whitman |
| 6,699,177 B1 | 3/2004 | Wang et al. |
| 6,716,233 B1 * | 4/2004 | Whitman ........................ 606/219 |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |

(Continued)

FOREIGN PATENT DOCUMENTS

| | | | |
|---|---|---|---|
| EP | 1 813 203 A2 | | 8/2007 |
| JP | 2011036677 A | * | 2/2011 |
| WO | WO 99/52489 | | 10/1999 |
| WO | WO 2007/003053 A2 | | 3/2007 |

*Primary Examiner* — Robert Long

(57) ABSTRACT

The present disclosure provides for a surgical instrument. The surgical instrument includes a handle portion and a body portion extending distally from the handle portion and defining a first longitudinal axis. The surgical instrument includes an articulating tool assembly defining a second longitudinal axis and having a proximal end. The articulating tool assembly is disposed at a distal end of the body portion and is configured to be articulated with respect to the body portion, namely, the articulating tool assembly is movable from a first position in which the second longitudinal axis is substantially aligned with the first longitudinal axis to at least a second position in which the second longitudinal axis is disposed at an angle with respect to the first longitudinal axis. The surgical instrument also includes an articulation mechanism configured to articulate the articulating tool assembly.

16 Claims, 4 Drawing Sheets

(56) References Cited

U.S. PATENT DOCUMENTS

| | | | |
|---|---|---|---|
| 6,981,628 B2 | 1/2006 | Wales | |
| 6,981,941 B2 * | 1/2006 | Whitman et al. | 600/1 |
| 7,032,798 B2 * | 4/2006 | Whitman et al. | 227/175.1 |
| 7,077,856 B2 | 7/2006 | Whitman et al. | |
| 7,193,519 B2 | 3/2007 | Root et al. | |
| 7,246,734 B2 | 7/2007 | Shelton, IV | |
| 7,303,107 B2 | 12/2007 | Milliman et al. | |
| 7,380,696 B2 | 6/2008 | Shelton, IV et al. | |
| 7,404,508 B2 | 7/2008 | Smith et al. | |
| 7,431,188 B1 | 10/2008 | Marczyk | |
| 7,431,189 B2 * | 10/2008 | Shelton et al. | 227/176.1 |
| 7,464,846 B2 | 12/2008 | Shelton, IV et al. | |
| 7,464,847 B2 * | 12/2008 | Viola et al. | 227/175.2 |
| 7,673,780 B2 * | 3/2010 | Shelton et al. | 227/175.1 |
| 7,717,312 B2 * | 5/2010 | Beetel | 227/175.1 |
| 7,922,061 B2 * | 4/2011 | Shelton et al. | 227/175.1 |
| 8,157,145 B2 * | 4/2012 | Shelton et al. | 227/175.1 |
| 2005/0006430 A1 | 1/2005 | Wales | |
| 2005/0131390 A1 * | 6/2005 | Heinrich et al. | 606/1 |
| 2006/0022015 A1 | 2/2006 | Shelton, IV et al. | |
| 2006/0212069 A1 * | 9/2006 | Shelton | 606/205 |
| 2007/0023477 A1 | 2/2007 | Whitman et al. | |
| 2007/0084897 A1 | 4/2007 | Shelton, IV et al. | |
| 2007/0102474 A1 | 5/2007 | Shelton, IV et al. | |
| 2007/0125826 A1 | 6/2007 | Shelton, IV | |
| 2007/0175949 A1 * | 8/2007 | Shelton et al. | 227/176.1 |
| 2007/0175951 A1 | 8/2007 | Shelton, IV et al. | |
| 2007/0175952 A1 | 8/2007 | Shelton, IV et al. | |
| 2007/0175953 A1 | 8/2007 | Shelton, IV et al. | |
| 2007/0175955 A1 | 8/2007 | Shelton, IV et al. | |
| 2007/0175956 A1 | 8/2007 | Swayze et al. | |
| 2007/0175957 A1 | 8/2007 | Shelton, IV et al. | |
| 2007/0175958 A1 | 8/2007 | Shelton, IV et al. | |
| 2007/0175959 A1 | 8/2007 | Shelton, IV et al. | |
| 2007/0175960 A1 | 8/2007 | Shelton, IV et al. | |
| 2007/0175962 A1 | 8/2007 | Shelton, IV et al. | |
| 2007/0175964 A1 | 8/2007 | Shelton, IV et al. | |
| 2007/0179408 A1 * | 8/2007 | Soltz | 600/587 |
| 2007/0187453 A1 | 8/2007 | Smith et al. | |
| 2008/0029570 A1 | 2/2008 | Shelton et al. | |
| 2008/0029572 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 * | 2/2008 | Shelton et al. | 227/176.1 |
| 2008/0029576 A1 | 2/2008 | Shelton et al. | |
| 2008/0029577 A1 | 2/2008 | Shelton et al. | |
| 2008/0048002 A1 | 2/2008 | Smith et al. | |
| 2008/0164296 A1 | 7/2008 | Shelton et al. | |
| 2008/0229571 A1 | 9/2008 | Acosta | |
| 2009/0090763 A1 * | 4/2009 | Zemlok et al. | 227/175.2 |
| 2009/0289096 A1 * | 11/2009 | Shelton et al. | 227/180.1 |
| 2010/0200637 A1 * | 8/2010 | Beetel | 227/175.1 |
| 2011/0017801 A1 * | 1/2011 | Zemlok et al. | 227/175.1 |
| 2011/0204119 A1 * | 8/2011 | McCuen | 227/175.1 |
| 2011/0301579 A1 * | 12/2011 | Marczyk et al. | 606/1 |

* cited by examiner

SAFETY METHOD FOR POWERED SURGICAL INSTRUMENTS

CROSS-REFERENCE TO RELATED APPLICATIONS

This application claims the benefit of and priority to U.S. Provisional Patent Application No. 61/234,377, filed Aug. 17, 2009, the entire disclosure of which is incorporated by reference herein.

BACKGROUND

1. Technical Field

The present disclosure relates to a surgical instrument, e.g., a linear stapler, having an articulating tool assembly. More particularly, the present disclosure relates to a surgical instrument which includes a mechanism for controlling and actuating an articulating surgical instrument.

2. Background of Related Art

Surgical instruments that include a tool assembly mounted on a distal end of a body portion of the surgical instrument for articulation are well known. Typically, such surgical instruments include articulation control mechanisms which allow an operator to remotely articulate the tool assembly in relation to the body portion of a surgical instrument. This allows the operator to more easily access, operate on, and/or manipulate tissue.

Such articulating tool assemblies have become desirable, especially in the endoscopic surgical procedures. In an endoscopic surgical procedure, the distal end of a surgical instrument is inserted through a small incision in the body to access a surgical site. Typically, an appropriately sized cannula, e.g., 5 mm, 10 mm, etc., is inserted through the body incision to provide a guide channel for accessing the surgical site.

Current known devices can typically require 10-60 pounds of manual hand force to clamp tissue and deploy and form surgical fasteners in tissue which, over repeated use, can cause a surgeon's hand to become fatigued. Gas powered pneumatic staplers which implant surgical fasteners into tissue are also known in the art. Certain of these instruments utilize a pressurized gas supply which connects to a trigger mechanism. The trigger mechanism, when depressed, simply releases pressurized gas to clamp tissue and implant fasteners into the tissue.

Motor-powered surgical staplers are also known in the art. These include powered surgical staplers having motors which activate staple firing mechanisms. However, these motor powered devices only provide for limited user control of the stapling process. The user can only toggle a single switch and/or button to actuate the motor and applies corresponding torque to the stapler's firing mechanisms. In certain other devices, a controller is used to control the stapler, which then powers the clamping and fastening processes.

There is a continual need for powered surgical staplers which include various sensors. The sensors provide relevant feedback to feedback controllers which automatically adjust various parameters of the powered stapler in response to sensed feedback signals representative of stapler operation, including articulation and actuation of the tool assemblies.

SUMMARY

The present disclosure provides for a surgical instrument. The surgical instrument includes a handle portion and a body portion extending distally from the handle portion and defining a first longitudinal axis. The surgical instrument includes an articulating tool assembly defining a second longitudinal axis and having a proximal end. The articulating tool assembly is disposed at a distal end of the body portion and is configured to be articulated with respect to the body portion, namely, the articulating tool assembly is movable from a first position in which the second longitudinal axis is substantially aligned with the first longitudinal axis to at least a second position in which the second longitudinal axis is disposed at an angle with respect to the first longitudinal axis. The surgical instrument also includes an articulation mechanism configured to articulate the articulating tool assembly.

In one embodiment, the articulation mechanism includes one or more switches for activating the articulation mechanism, wherein the switches activate the articulation mechanism after being engaged for a predetermined period of time. The articulation mechanism may also include two or more switches which are configured to be operated concurrently to activate the articulation mechanism. In another embodiment, the articulation mechanism includes a stop switch, which when actuated is configured to disable the articulation mechanism.

The surgical instrument also includes a controller and one or more lock-out sensors coupled to the articulation mechanism. The sensors are configured to determine when the articulating tool assembly has engaged tissue. The sensors then transmit a signal to the controller to prevent further articulation of the tool assembly.

The controller is also configured to provide multiple commands to the articulation mechanism for controlling the articulation of the tool assembly. The controller may provide a first articulation command to the articulation mechanism to articulate the tool assembly in a first direction. The controller may then provide a second articulation command, which interrupts the first articulation command and signals the articulation mechanism to articulate the tool assembly in a second direction.

According to one embodiment of the present disclosure, a powered surgical instrument is disclosed. The instrument includes a handle portion, a body portion extending distally from the handle portion and defining a first longitudinal axis and an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis. The instrument also includes an articulation mechanism configured to articulate the articulating tool assembly, wherein the articulation mechanism includes a motor operatively coupled to the articulating tool assembly, a controller electrically coupled to the motor and configured to control operation of the motor and at least one switch coupled to the controller, wherein the at least one switch is configured to signal the controller to activate the articulation mechanism in response to the at least one switch being engaged for a predetermined period of time.

According to another embodiment of the present disclosure, a powered surgical instrument is disclosed. The instrument includes a handle portion, a body portion extending distally from the handle portion and defining a first longitudinal axis and an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis. The instrument also includes an articulation mechanism configured to articulate the articulating tool assembly, wherein the articulation mechanism includes a motor operatively coupled to the articulating tool assembly, a controller electrically coupled to the motor and configured to control operation of the motor, and a first switch and a second switch coupled to the controller, wherein concurrent engagement of the first and second switches signals the controller to activate the articulation mechanism.

According to a further embodiment of the present disclosure an articulation mechanism configured to articulate an articulating tool assembly is disclosed. The articulation mechanism includes a motor operatively coupled to an articulating tool assembly, a controller electrically coupled to the motor and configured to control operation of the motor, and a first switch and a second switch coupled to the controller, wherein the controller activates the articulation mechanism in response to the first and second switches being concurrently engaged for a predetermined period of time.

BRIEF DESCRIPTION OF THE DRAWINGS

Various embodiments of the subject instrument are described herein with reference to the drawings wherein.

DETAILED DESCRIPTION

Figure 1:
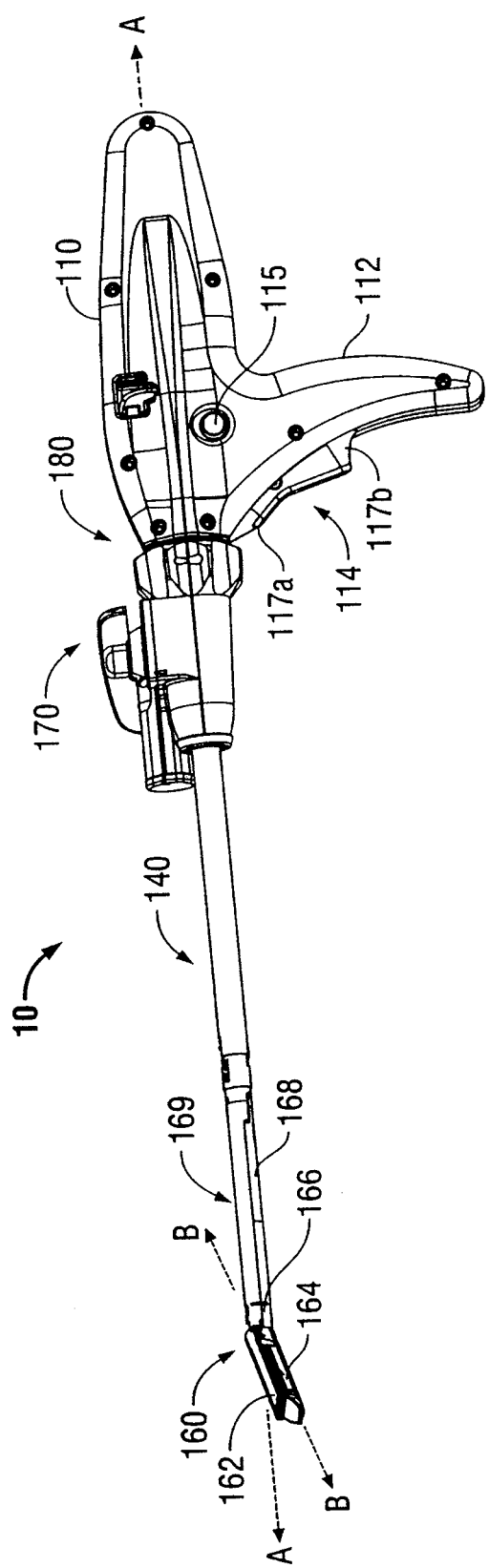
FIG. 1 is a perspective view of a powered surgical instrument according to an embodiment of the present disclosure.

Embodiments of the presently disclosed powered surgical instrument are now described in detail with reference to the drawings, in which like reference numerals designate identical or corresponding elements in each of the several views. As used herein the term "distal" refers to that portion of the powered surgical instrument, or component thereof, farther from the user while the term "proximal" refers to that portion of the powered surgical instrument or component thereof, closer to the user.

A powered surgical instrument, e.g., a surgical stapler, in accordance with the present disclosure is referred to in the figures as reference numeral 10. Referring initially to FIG. 1, powered surgical instrument 10 includes a housing 110, an endoscopic portion 140 defining a first longitudinal axis A-A extending therethrough, and an articulating tool assembly (e.g., end effector 160), defining a second longitudinal axis B-B extending therethrough. Endoscopic portion 140 extends distally from housing 110 and the end effector 160 is disposed adjacent a distal portion of endoscopic portion 140. In an embodiment, the components of the housing 110 are sealed against infiltration of particulate and/or fluid contamination and help prevent damage of the components by sterilization processes.

According to an embodiment of the present disclosure, end effector 160 includes a first jaw member having one or more surgical fasteners (e.g., cartridge assembly 164) and a second opposing jaw member including an anvil portion for deploying and forming the surgical fasteners (e.g., an anvil assembly 162). In certain embodiments, the staples are housed in cartridge assembly 164, which is configured to apply linear rows of staples to body tissue either in simultaneous or sequential manner. Either one or both of the anvil assembly 162 and the cartridge assembly 164 are movable in relation to one another between an open position, in which the anvil assembly 162 is spaced from cartridge assembly 164, and an approximated or clamped position, in which the anvil assembly 162 is in juxtaposed alignment with cartridge assembly 164.

It is further envisioned that end effector 160 is attached to a mounting portion 166, which is pivotably attached to a body portion 168. Body portion 168 may be integral with endoscopic portion 140 of powered surgical instrument 10, or may be removably attached to the instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may be connectable to endoscopic portion 140 through a bayonet connection. It is envisioned that the loading unit 169 has an articulation link connected to mounting portion 166 of the loading unit 169 and the articulation link is connected to a linkage rod 220 (FIG. 4) so that the end effector 160 is articulated as the linkage rod 220 is translated in the distal-proximal direction along first longitudinal axis A-A as discussed in more detail below. Other means of connecting end effector 160 to endoscopic portion 140 to allow articulation may be used, such as a flexible tube or a tube comprising a plurality of pivotable members.

The loading unit 169 may incorporate or be configured to incorporate various end effectors, such as vessel sealing devices, linear stapling devices, circular stapling devices, cutters, graspers, etc. Such end effectors may be coupled to endoscopic portion 140 of powered surgical instrument 10. An intermediate flexible shaft may be included between handle portion 112 and loading unit. It is envisioned that the incorporation of a flexible shaft may facilitate access to and/or within certain areas of the body.

Figure 2:
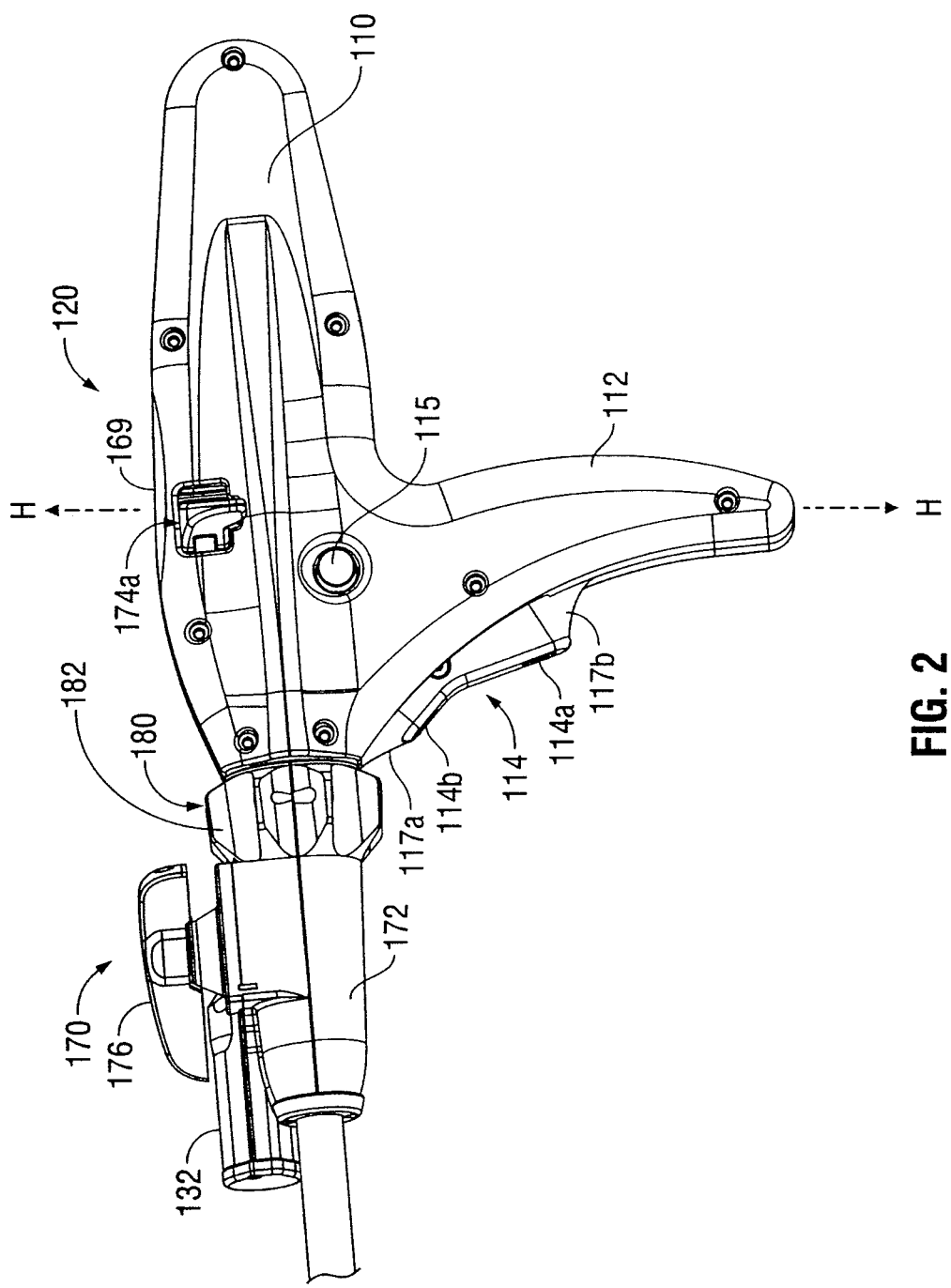
FIG. 2 is a partial enlarged perspective view of the powered surgical instrument of FIG. 1 according to an embodiment of the present disclosure.

With reference to FIGS. 1 and 2, an enlarged view of the housing 110 is illustrated according to an embodiment of the present disclosure. In the illustrated embodiment, housing 110 includes a handle portion 112 having a main drive switch 114 disposed thereon. The switch 114 may include first and second switches 114a and 114b formed together as a toggle switch. The handle portion 112, which defines a handle axis H-H, is configured to be grasped by fingers of a user. The handle portion 112 has an ergonomic shape providing ample palm grip leverage which prevents the handle portion 112 being squeezed out of the user's hand during operation. Each switch 114a and 114b is shown as being disposed at a suitable location on handle portion 112 to facilitate its depression by a user's finger or fingers.

Figure 4:
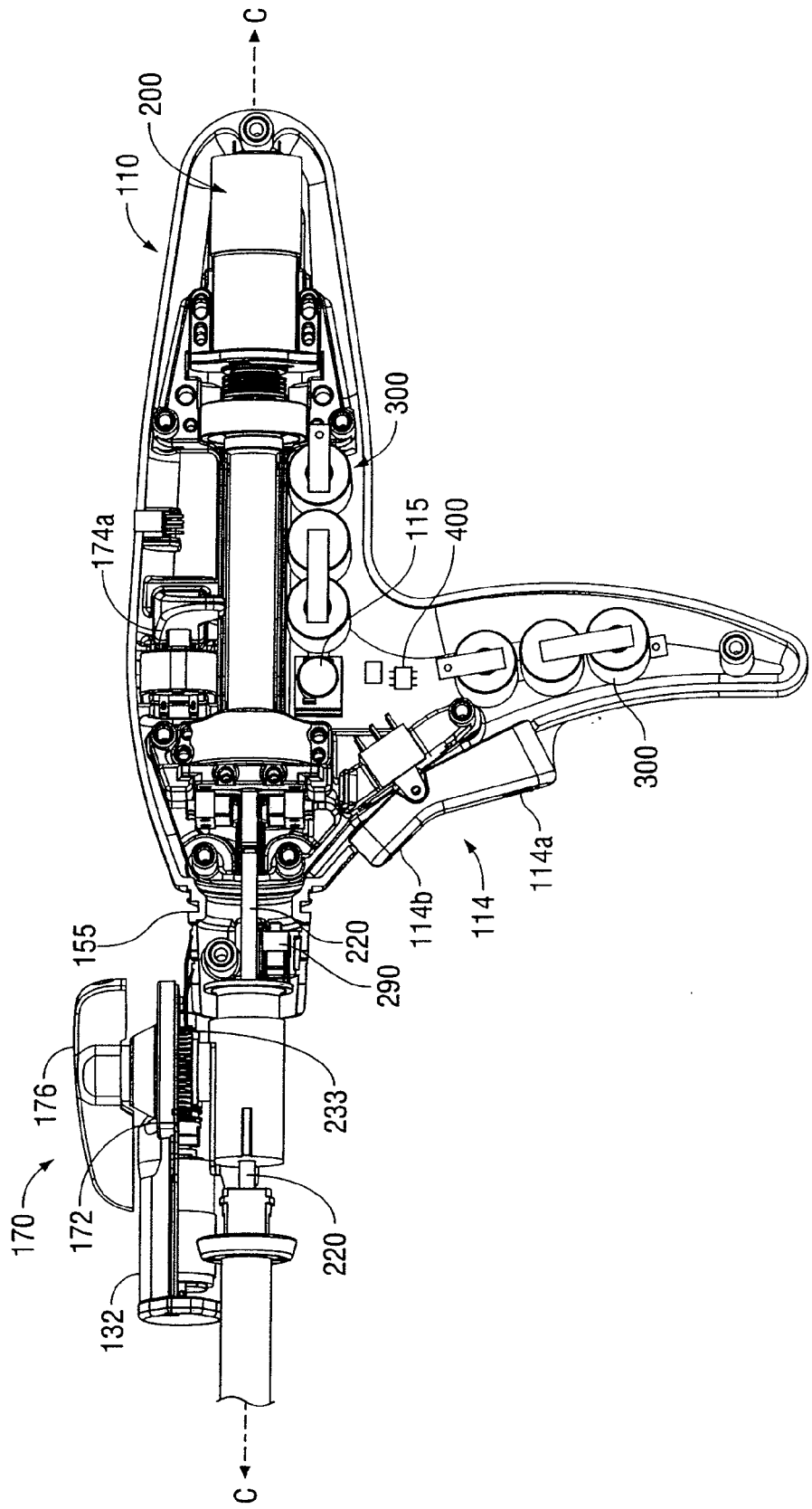
FIG. 4 is a partial perspective sectional view of internal components of the powered surgical instrument of FIG. 1 according to an embodiment of the present disclosure.

Additionally, and with reference to FIGS. 1 and 2, switches 114a, 114b may be used for starting and/or stopping movement of drive motor 200 coupled to a power source 300 (FIG. 4). In one embodiment, the switch 114a is configured to activate the drive motor 200 in a first direction to advance a firing rod (not shown) in a distal direction thereby approximating the anvil and the cartridge assemblies 162 and 164. Conversely, the switch 114b may be configured to retract the firing rod to open the anvil and cartridge assemblies 162 and 164 by activating the drive motor 200 in a reverse direction. The retraction mode initiates a mechanical lock out, preventing further progression of stapling and cutting by the loading unit 169. The toggle has a first position for activating switch 114a, a second position for activating switch 114b, and a neutral position between the first and second positions. Similar retraction mechanisms are disclosed in a commonly-owned U.S. Pat. No. 7,303,107 by Milliman et al., the entire disclosure of which is incorporated by reference herein.

The housing 110, in particular the handle portion 112, includes switch shields 117a and 117b. The switch shields 117a and 117b may have a rib-like shape surrounding the bottom portion of the switch 114a and the top portion of the switch 114b, respectively. The switch shield 117a and 117b prevent accidental activation of the switch 114. Further, the switches 114a and 114b have high tactile feedback requiring increased pressure for activation.

In one embodiment, the switches 114a and 114b are configured as multi-speed (e.g., two or more), incremental or variable speed switches which control the speed of the drive motor 200 and the firing rod in a non-linear manner. For example, switches 114a, 114b can be pressure-sensitive. This type of control interface allows for gradual increase in the rate of speed of the drive components from a slower and more precise mode to a faster operation.

The switches 114a and 114b are coupled to a non-linear speed control circuit which can be implemented as a voltage regulation circuit, a variable resistance circuit, or a microelectronic pulse width modulation circuit. The switches 114a and 144b may interface with the control circuit by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a and 114b to operate the drive motor 200 in multiple speed modes, such as continuously increasing the speed of the drive motor 200 either incrementally or gradually depending on the type of the control circuit being used, based on the depression of the switches 114a and 114b.

Figure 3:
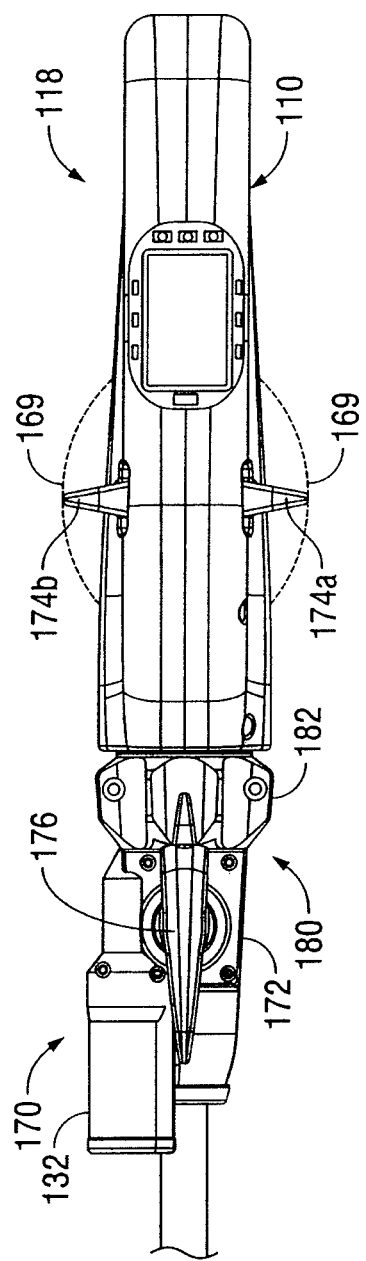
FIG. 3 is a partial enlarged plan view of the powered surgical instrument of FIG. 1 according to an embodiment of the present disclosure.

FIGS. 2-4 illustrate an articulation mechanism 170, including an articulation housing 172, powered articulation switches 174a and 174b, an articulation motor 132 coupled to the power source 300 and a manual articulation knob 176. The switches 174a and 174b have a paddle-type shape. The articulation switches 174a and 174b provide for powered articulation of the end effector 160 and the manual articulation knob 176 provides for manual articulation. Engagement and/or translation of the powered articulation switches 174a and 174b or pivoting of the manual articulation knob 176 activates the articulation motor 132 which then actuates an articulation gear 233 of the articulation mechanism 170 as shown in FIG. 4. The articulation gear 233 is, in turn, operatively coupled to the linkage rod 220. More specifically, the articulation mechanism 170 moves the linkage rod 220 in a distal or proximal direction along the longitudinal axis A-A, which imparts articulating motion to the end effector 160. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A in either direction with respect to the longitudinal axis A-A. The powered articulation switches 174a and 174b may also incorporate similar non-linear speed controls as the clamping mechanism that is controlled by the switches 114a and 114b.

With reference to FIGS. 2 and 3, the housing 110 includes switch shields 169 having a wing-like shape and extending from the top surface of the housing 110 over the switches 174a and 174b. The switch shields 169 prevent accidental activation of the switches 174a and 174b and require the user to reach below the shield 169 in order to activate the articulation mechanism 170.

Further details of articulation housing 172, powered articulation switches 174a and 174b, manual articulation knob 176 and providing articulation to end effector 160 are described in detail in commonly-owned U.S. Pat. No. 7,431,188 to Marczyk, the contents of which are hereby incorporated by reference in their entirety. It is envisioned that any combinations of limit switches, proximity sensors (e.g., optical and/or ferromagnetic), linear variable displacement transducers and shaft encoders which may be disposed within housing 110, may be utilized to control and/or record an articulation angle of end effector 160 and/or position of the linkage rod 220.

As shown in FIG. 4, the instrument 10 also includes a controller 400 electrically coupled to the motor 200 and various sensors disposed in the instrument 10. The sensors detect various operating parameters of the instrument 10 (e.g., linear speed, rotation speed, articulation position, temperature, battery charge, and the like), which are then reported to the controller 400. The controller 400 may then respond accordingly to the measured operating parameters (e.g., adjust the speed of the motor 200, control articulation angle, shut-off the power supply, report error conditions, etc.).

The controller 400 is coupled to the switch 114 and the switches 174a and 174b to control the motors 200 and 132, respectively. The switches 174a and 174b may be configured to operate the articulation mechanism 170 in a plurality of modes. In another embodiment, the switches 174a and 174b may be slidably disposed on one or more guide rails within the housing 110. The switches 174a and 174b may be mechanically and/or electrically linked such that the articulation mechanism 170 is activated by toggling the switches 174a and 174b in tandem.

The switches 174a and 174b may be disposed about a pivot (e.g., common or separate pivots) and may be actuated by rotation thereof about the pivot. The articulation of the end effector 160 may be accomplished by engaging and moving the switches 174a and 174b in a direction corresponding to a desired articulation direction. More specifically, to articulate the end effector 160 in a clockwise direction the switches 174a and 174b are also moved in a clockwise direction, namely, the switch 174a is moved in the proximal direction and the switch 174b is moved in a distal direction. To articulate the end effector 160 in a counterclockwise direction the switches 174a and 174b are also moved in a counterclockwise direction, namely, the switch 174a is moved in the distal direction and the switch 174b is moved in a proximal direction. This configuration provides for a natural association between the motion of the switches 174a and 174b and the end effector 169, such that the pulling one of the switches 174a and 174b in a proximal direction pulls the end effector 169 toward the corresponding side and pushing one of the switches 174a and 174b in a distal direction pushes the end effector 169 therefrom.

In embodiments, the switches may be engaged in the same direction, such as for example, pushing on the switches 174a and 174b in the proximal direction to articulate the end effector 169 in one direction (e.g., clockwise) and pulling on the switches 174a and 174b in the distal direction to articulate the end effector 169 in the opposite direction (e.g., counterclockwise).

In embodiments, the switches 174a and 174b may be independently movable such that the articulation mechanism 170 may be activated by toggling either of the switches 174a and 174b. In either of the configurations, the switches 174a and 174b may be delayed activation switches such that the switches 174a and 174b have to be engaged continuously for a predetermined period of time (e.g., from about 1 second to about 5 seconds) to activate the articulation mechanism 170.

This may be accomplished by coupling the switches 174a and 174b to the controller 400, which tracks the engagement period of time. Once the engagement period exceeds the predetermined period of time, the controller 400 activates the articulation mechanism 170.

In another illustrative embodiment, the switches 174a and 174b may be independently movable and configured to activate the articulation mechanism 170 upon concurrent engagement thereof. More specifically, both of the switches 174a and 174b are toggled in the desired direction prior to the controller 400 activating the articulation mechanism 170. The controller 400 listens for activation signals from both of the signals prior to activation. In one embodiment, the controller 400 also ensures that the engagement of both of the switches 174a and 174b corresponds to the same desired articulation motion (e.g., pulling on the switch 174a while pushing on the switch 174b and vice versa) prior to signaling the motor 132. In this configuration, engagement of only one of the switches 174a and 174b or engagement of the switches 174a and 174b in the same direction does not trigger the activation of the articulation mechanism. This feature may be combined with the delayed activation switching discussed above, such that the both of the switches 174a and 174b have to be engaged concurrently for a predetermined period of time prior to the controller 400 activating the articulation mechanism 170.

The switches 174a and 174b are also configured to provide signals to the controller 400 after an initial articulation command has been processed. This allows the controller 400 to interrupt the previously issued command and then signal the articulation mechanism 170 to reverse the articulation motion. This feature may be combined with the dual-activation configuration discussed above, such that the reverse command is not transmitted by the controller 400 unless both of the switches 174a and 174b are engaged for a predetermined period of time. More specifically, engagement of the switches 174a and 174b in a first orientation (e.g., pulling on the switch 174a while pushing on the switch 174b) for a predetermined period of time signals the controller 400 to articulate the end effector 160 in a first direction. Engagement of the switches 174a and 174b in a second orientation (e.g., pushing on the switch 174a while pulling on the switch 174b) for a predetermined period of time signals the controller 400 to articulate the end effector 160 in a second direction opposite of the first direction.

With respect to FIGS. 2 and 4, the instrument 10 also includes a stop switch 115 that is configured to interrupt the currently activated articulation command. The switch 115 is also coupled to the controller 400 and engagement of the switch 115 signals the controller 400 to issue a stoppage command to the motor 132 such that current articulation command is interrupted. In one embodiment, the switch 115 may also be configured for delayed activation switching, such that the switch 115 has to be engaged for a predetermined period of time prior to the controller 400 deactivating the articulation mechanism 170.

In addition to manual deactivation and interruption of the articulation processes, it is also envisioned that an automatic interlock may also be utilized. With reference to FIG. 4, the instrument 10 includes a lock-out sensor 290 electrically coupled to the controller 400. The lock-out sensor 290 is disposed within the housing 110 in proximity with the linkage rod 220 and is configured to determine a longitudinal position of the linkage rod 220. The lock-out sensor 290 may be any type of a linear position sensor suitable for determining linear displacement of the linkage rod 220 such as a potentiometer, a proximity sensor (e.g., optical and/or ferromagnetic), a linear variable displacement transducer, a shaft encoders, a Hall-effect sensor and the like. The lock-out sensor 290 determines when the end effector 160 is engaged, i.e., when the first and second opposing jaw members of the end effector 160 are grasping the tissue by measuring the displacement of the linkage rod 220. Once the linkage rod 220 is moved distally passed a predetermined point, the jaw members are engaged and tissue is grasped therebetween. Therefore, the lock-out sensor 290 measures distal displacement of the linkage rod 220 and signals the controller 400 once the jaw members are engaged, in response to which, the controller 400 prevents activation of the articulation mechanism 170 by ignoring any articulation commands from the switches 174a and 174b. Accidental engagement of the articulation mechanism 170 may damage the instrument 10 and more importantly may cause injury to the patient. The use of the lock-out sensor 290 in combination with the controller 400 prevents such accidental misuse of the articulation mechanism 170.

It will be understood that various modifications may be made to the embodiments shown herein. Therefore, the above description should not be construed as limiting, but merely as exemplifications of preferred embodiments. Although specific features of the powered surgical instrument are shown in some of the drawings and not in others, this is for convenience only as each feature may be combined with any or all of the other features in accordance with the aspects of the present disclosure. Other embodiments will occur to those skilled in the art and are within the following claims.

What is claimed is:

1. A powered surgical instrument comprising:
   a handle portion;
   a body portion extending distally from the handle portion and defining a first longitudinal axis;
   an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
   an articulation mechanism configured to articulate the articulating tool assembly, wherein the articulation mechanism includes:
   a motor operatively coupled to the articulating tool assembly;
   a controller electrically coupled to the motor and configured to control operation of the motor; and
   at least one switch coupled to the controller, wherein the at least one switch is configured to signal the controller to activate the articulation mechanism in response to the at least one switch being engaged for a period of time having a duration in the range of about one second to about five seconds.

2. The powered surgical instrument according to claim 1, wherein the at least one switch is engaged in a direction corresponding to a desired articulation direction.

3. The powered surgical instrument according to claim 1, wherein the articulation mechanism further includes a plurality of switches configured to be engaged concurrently to activate the articulation mechanism.

4. The powered surgical instrument according to claim 1, wherein the articulation mechanism further includes a stop switch configured to disable the articulation mechanism.

5. The powered surgical instrument according to claim 1, wherein the controller is configured to activate the articulation mechanism in response to a first command and to interrupt the activation of the articulation mechanism in response to a second command.

6. The powered surgical instrument according to claim 1, wherein the articulation mechanism further includes a lock-out sensor electrically coupled to the controller and configured to determine engagement of the articulating tool assembly with tissue, wherein the lock-out sensor prevents activation of the articulation mechanism.

7. A powered surgical instrument comprising:
a handle portion;
a body portion extending distally from the handle portion and defining a first longitudinal axis; an articulating tool assembly defining a second longitudinal axis and having a proximal end, the articulating tool assembly disposed at a distal end of the body portion and being movable from a first position in which the second longitudinal axis is substantially aligned with the first longitudinal axis to at least a second position in which the second longitudinal axis is disposed at an angle with respect to the first longitudinal axis; and
an articulation mechanism configured to articulate the articulating tool assembly, wherein the articulation mechanism includes:
a motor operatively coupled to the articulating tool assembly;
a controller electrically coupled to the motor and configured to control operation of the motor; and
a first switch and a second switch coupled to the controller, wherein concurrent engagement of the first and second switches for a period of time of about one second to about five seconds signals the controller to activate the articulation mechanism.

8. The powered surgical instrument according to claim 7, wherein the first switch and the second switch are engaged in a direction corresponding to a desired articulation direction.

9. The powered surgical instrument according to claim 7, wherein the articulation mechanism further includes a stop switch configured to disable the articulation mechanism.

10. The powered surgical instrument according to claim 7, wherein the controller is configured to activate the articulation mechanism in response to a first command and to interrupt the activation of the articulation mechanism in response to a second command.

11. The powered surgical instrument according to claim 7, wherein the articulation mechanism further includes a lock-out sensor electrically coupled to the controller and configured to determine engagement of the articulating tool assembly with tissue, wherein the lock-out sensor prevents activation of the articulation mechanism.

12. An articulation mechanism configured to articulate an articulating tool assembly, the articulation mechanism comprising:
a motor operatively coupled to an articulating tool assembly;
a controller electrically coupled to the motor and configured to control operation of the motor; and
a first switch and a second switch coupled to the controller, wherein the controller activates the articulation mechanism in response to the first and second switches being concurrently engaged for a period of time having a duration in the range of about one second to about five seconds.

13. The articulation mechanism according to claim 12, wherein the first switch and the second switch are engaged in a direction corresponding to a desired articulation direction.

14. The articulation mechanism according to claim 12, further comprising a stop switch configured to disable the articulation mechanism.

15. The articulation mechanism according to claim 12, wherein the controller is configured to activate the articulation mechanism in response to a first command and to interrupt the activation of the articulation mechanism in response to a second command.

16. The articulation mechanism according to claim 12, further comprising:
a lock-out sensor electrically coupled to the controller and configured to determine engagement of the articulating tool assembly with tissue, wherein the lock-out sensor prevents activation of the articulation mechanism.

* * * * *